United States Patent [19]

Bronte et al.

[11] Patent Number: 4,659,220
[45] Date of Patent: Apr. 21, 1987

[54] OPTICAL INSPECTION SYSTEM FOR SEMICONDUCTOR WAFERS

[75] Inventors: Joseph J. Bronte, Poughkeepsie; Roland C. Herbert, Hopewell Junction; Henri A. Khoury, Yorktown Heights, all of N.Y.

[73] Assignee: International Business Machines Corporation, Armonk, N.Y.

[21] Appl. No.: 663,292

[22] Filed: Oct. 22, 1984

[51] Int. Cl.⁴ .............................................. G01N 21/55
[52] U.S. Cl. ..................... 356/237; 358/106
[58] Field of Search ............... 356/72, 73, 237; 250/562, 563, 572; 358/106; 382/8, 34

[56] References Cited

U.S. PATENT DOCUMENTS

| | | | |
|---|---|---|---|
| 4,056,716 | 11/1977 | Baxter et al. | 364/515 |
| 4,200,861 | 1/1980 | Hubach et al. | 382/34 |
| 4,314,763 | 2/1982 | Steigmeir et al. | 356/237 |
| 4,342,515 | 8/1982 | Akiba et al. | 356/237 |
| 4,376,583 | 3/1983 | Alford et al. | 356/237 |
| 4,377,340 | 3/1983 | Green et al. | 356/237 |
| 4,449,818 | 5/1984 | Yamaguchi et al. | 356/237 |
| 4,555,798 | 11/1985 | Broadbent et al. | 356/237 |

OTHER PUBLICATIONS

"High-Resolution Computer-Controlled Television System for Hybrid Circuit Inspection", Arlan et al., SPIE, 1979, pp. 130-139.

IBM TDB, Nov. '81, p. 3059; Automatic Inspection and Computation Tool of Patterned Semiconductor Wafers; M. Barret.

IBM TDB, May '83, pp. 6558-6559; Defects Detection by Spacial Correlation of Images, N. Begnoche.

*Primary Examiner*—Davis L. Willis
*Assistant Examiner*—S. A. Turner
*Attorney, Agent, or Firm*—Anne Vachon Dougherty

[57] ABSTRACT

A method and apparatus for automatically detecting defects on the surfaces of semiconductor wafers and chips which provides a 100% inspection capability. The entire surface of each wafer is scanned by use of a low magnification, low resolution detector such as a photodiode array. Whenever a defect occurs, encoders on the supporting XY table are triggered, such that the location of a defect on the wafer is recorded. After the event coordinates have been determined, the XY table positions each defect directly under a high magnification detector to determine the nature of the detected event. Since only the locations of the detected events are stored, 100% of the processed wafers can be scanned for defects.

3 Claims, 3 Drawing Figures

OPTICAL INSPECTION SYSTEM FOR SEMICONDUCTOR WAFERS

BACKGROUND OF THE INVENTION

1. Technical Field

This invention relates to the field of optical inspection of semiconductor wafers.

2. Background Art

As manufacturers attempt to tighten ground rules while maintaining device integrity, the elimination of defects in processed semiconductor wafers has become increasingly important. Typically, these defects include discontinuities in the metallization layers as well as particulate contaminants.

Conventionally, in order to eliminate these defects (as well as prevent the shipment of faulty wafers), several of the processed wafers are examined by use of an optical monitoring system. In such optical monitoring systems, a light beam is projected onto the surface of the processed wafer, the wafer reflects the incident light, and the reflected light impinges on a lens system. If defects are present on the wafer, there is a corresponding change in the intensity of the reflected light.

Typically, the reflected light is converted into an electrical signal which is subsequently converted into a visible image on a display screen. By viewing the display screen, an operator can determine the existence of defects on the surface of the semiconductor wafer.

It has been found that the foregoing inspection technique presents several difficulties. First, since reliance is placed upon the operator to detect defects, the inspection takes a relatively long time to complete. If such an inspection were to be carried out on all of the processed wafers, astronomical cost inefficiencies would result. In practice, this detection procedure is carried out on only a small percentage (on the order of 5–10%) of the processed wafers. Such a procedure is grossly inefficient, in that 90–95% of the processed wafers are not tested. Second, in the monitoring system as described above, the resultant electrical signal is representative of the entire surface of the wafer. If this signal were to be digitized and stored for a large number of wafers, the storage required would be quite large.

U.S. Pat. No. 4,376,583 (issued 3/15/83 to Alford et al) discloses an inspection scanning system which does not rely on manual inspection in order to detect defects on the surface of a processed wafer. The inspected wafers are automatically sorted into separate categories according to the nature of the detected defect (if any). Light reflected from the surface of the wafer is compared to various threshold levels to produce a seven-bit address signal. This signal is applied to a flow handling logic network, which is used to construct a digital surface map of the wafer under inspection. The wafer is divided into a plurality of unit areas. Each of these unit areas is assigned a binary flaw code which represents the most severe flaw encountered within the unit area. An algorithm for grading each inspected wafer compares the accumulated number of stored flaw codes to a series of predetermined number and type ranges. The wafers are sorted as a function of where the stored flaws fall within these ranges. The stored flaw codes can also be used to visually display the occurrences of flaws on each inspected wafer as well as to print a map or a histogram of each wafer.

In the inspection scanning system as described above, the occurrence of defects is automatically determined by comparing a derived electrical signal to a series of threshold values. This eliminates the inefficiencies produced by manual inspection of a display screen. However, as in previously-described monitoring systems, the electrical signal produced by the optical inspection system of the Alford patent is representative of the total surface area of the wafer under test. Thus, if the Alford device were used to store representations of the defects on 100% of the processed wafers, the same impractical storage requirements would be presented.

Thus, a need has developed in the semiconductor processing art to provide an automatic defect (or "event") detection system which (a) scans all of the processed wafers in a time efficient manner, and (b) stores representations of the locations of all of the events on 100% of the processed wafers without the use of excessive memory capacity.

DISCLOSURE OF THE INVENTION

It is thus an object of the present invention to provide an improved system for automatically detecting the defects on a processed semiconductor wafer.

It is another object of the invention to provide a defect detection system which can be used to monitor 100% of the processed wafers.

The foregoing and other objects of the invention are realized by an automatic defect detection system which records the locations of defects on 100% of the processed wafers. Each semiconductor wafer is scanned, using an automated XY table, by a low magnification event detector. When an event is detected, the output of the positional tracking circuitry of the XY table is sampled such that the location of the event is stored. After the wafer has been completely scanned, the XY table positions the wafer under a high magnification viewer in accordance with the stored event location coordinates. A two-part analysis is then performed in order to verify the existence of events and to characterize the events as particulate contaminants or pattern defects.

BRIEF DESCRIPTION OF THE DRAWING

The structures and teachings of the present invention will become more apparent upon a description of the best mode for carrying out the invention. In the description to follow, reference will be made to the accompanying drawing, in which.

BEST MODE FOR CARRYING OUT THE INVENTION

Figure 1:
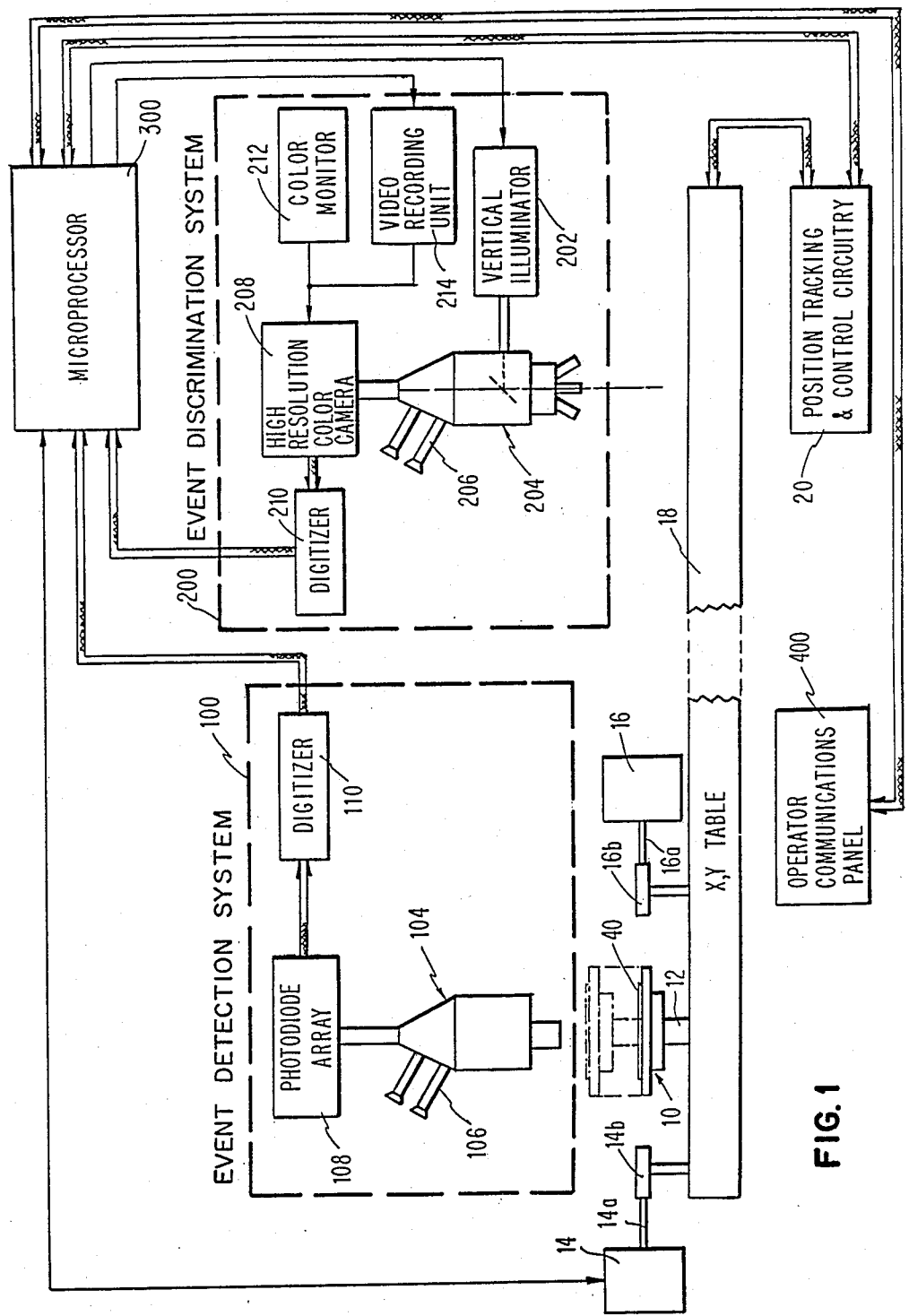
FIG. 1 is a schematic view of the automatic defect detection system of the invention.

Referring to FIG. 1, a processed wafer 40 is mounted on a vacuum chuck 10 which is supported by an elevator shaft 12. Wafer 40 is conveyed to chuck 10 by a conveyor (not shown) which automatically unloads the wafer from a storage cassette (not shown). When the wafer is conveyed to chuck 10, the chuck is in an elevated position as shown in dashed lines. Once the wafer is mounted on the chuck, the chuck is lowered to the position as shown in solid lines in FIG. 1.

Figure 2:
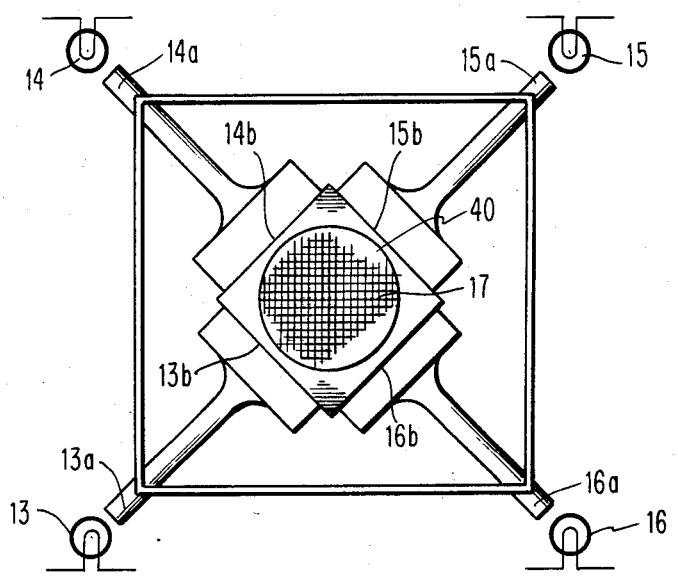
FIG. 2 is a top view of the grazing angle illumination system.

After vacuum chuck 10 lowers wafer 40 into position, the "grazing angle illuminator" is activated. As seen in FIG. 2, the grazing angle illuminator includes a series of light sources 13-16. Light from sources 13-16 is transmitted via respective fiber optic cables 13a-16a to respective slits 13b-16b, arranged in a square about the periphery of the wafer. The slits 13b-16b are oriented above the wafer at an angle between 0° and 5° with respect to the plane of the wafer. The wafer 40 is rotated such that the metal connecting lines 17 and other structures on the upper surface of the wafer are oriented at 45° with respect to the sides of the square defined by the light sources. The metal layers, etc., will reflect light at the grazing angle (i.e. 0°-5°), due to their rectilinear geometries. However, since "events" (i.e. pattern defects or particulate contaminants) tend to be non-rectilinear, they will scatter light in all directions. Thus, when viewed through eyepieces 106 of the event detection system 100 shown in FIG. 1, the events appear as specks of light in an otherwise dark background.

Event detection system 100 includes low magnification optics 104, eyepieces 106, a light sensitive pick-up head 108, and a digitizer 110. The image of wafer 40 is processed through low magnification optics 104 (e.g., a low-power microscope), such that a magnified image of a portion of wafer 40 is sent to light sensitive pick-up head 108. Eyepieces 106 are used for manual alignment of wafer 40 with respect to the grazing angle illuminator. The pick-up head 108, which is a photosensitive diode array or a vidicon tube, converts the image into electrical output signals which are digitized by digitizer 110 into one of 256 discrete intensity levels. When a defect occurs in the wafer, the scattered light alters the intensity of the image as sensed by pick-up head 108. Thus, when an event occurs, the digitized signal (i.e., the output signal from digitizer 110) will assume a different level.

The output signal of digitizer 110 is sent to a microprocessor 300. The microprocessor 300 has comparison circuits which compare the level of the digitized signal to predetermined high and low threshold values. If an event is present on the wafer, the level of the digitized signal will rise above the predetermined high threshold value. Conversely, if the wafer is event-free, the level of the digitized signal will fall below the low threshold value.

If the level of the digitized signal from digitizer 110 falls between the predetermined high and low threshold values, a discrimination procedure is invoked. By use of this procedure, ambiguous areas of the wafer surface are examined more closely in order to determine whether or not an event is present. When the level of the signal from digitizer 110 falls between the two thresholds (i.e., within the "gray zone"), microprocessor 300 outputs a control signal to the grazing angle illuminator light sources. This control signal incrementally raises or lowers the light sources with respect to the surface of wafer 40. This incremental motion causes the grazing angle to vary between 0° and 5°. Each time the illumination system moves, the signal from pick-up head 108 is redigitized and compared to the threshold values in microprocessor 300. If the level of the digitized signal rises above the high threshold value during this process, an event will be recorded. If the signal has not exceeded the high threshold value at the completion of this discrimination procedure, the wafer will be assumed to be event free. The illumination system is then returned to its original position for inspection of the next portion of the wafer.

After a given portion of wafer 40 is examined for defects, XY table 18 is moved to the next X, Y coordinate position. This incremental motion and analysis continues until the entire surface of wafer 40 has been scanned. In this manner, sequential locations along the surface of the wafer are scanned by event detector 100. The coordinate position of the XY table 18 is tracked via closed loop encoder feedback circuits 20. The output of these circuits provide electrical signals indicative of the exact position of the table. If an event is detected, these position signals are read into a RAM within microprocessor 300.

When the operator initially loads the wafer onto vacuum chuck 10, he enters a wafer identification code via an operator communications panel 400. Microprocessor 300 correlates the identification of the wafer with the detected events. In addition, prior to storing the X, Y event address signals, microprocessor 300 adds the X, Y displacement between the optical axis of event detection system 100 and the optical axis of event discrimination system 200. The purpose of this addition is discussed below. The modified X, Y event address signals are stored in the RAM along with the wafer identification code.

The event detection operation is continued until the entire surface of the wafer 40 has been scanned. Typically, the optics 104 of the event detection system 100 define a field of view on the order of one inch in width (approximately 25.4 milimeters). Each wafer has a diameter of 125 millimeters (i.e., approximately 5 inches). Thus, each wafer is completely scanned by five passes in the X direction. The wafer could be scanned in an "on the fly" mode; that is, during each pass in the X direction, the XY table 18 moves in a continuous manner. Preferably, the wafer is scanned in a "step and repeat" mode; that is, during each pass in the X direction, the XY table 18 is stepped so that a discrete number of chips on the wafer are viewed by event detection system 100. Since all of the wafers in a given lot have the same surface area, the same X, Y motion of table 18 can be used to scan all of the wafers. Thus, positional control of X, Y table 18 during scanning can be accomplished by use of a simple address counter algorithm which sequentially calculates subsequent X, Y coordinate positions control signals and reads out corresponding X, Y position control signals. When the address counter reaches a predetermined count, it could be reset to zero in order to scan the next wafer. At the same time, positional control of the XY table will be transferred so that the X, Y address signals are now read out of the RAM which stores the event position signals.

The first X, Y signal from the RAM causes the XY table 18 to move the wafer from its final scanning position beneath the optical axis of event detection system 100 such that the indicated event location along the wafer is positioned within the optical axis of event discrimination system 200. The purpose of event discrimination system 200 is to discern the nature of the events detected by event detection system 100.

Event discrimination system 200 comprises a high power microscope 204 having a vertical illuminator 202 and inspection eyepieces 206; a high resolution color camera 208 for converting the image from high power microscope 204 into corresponding electrical signals; color monitor 212 and video recording unit 214 for monitoring and recording, respectively, the electrical signals from camera 208; and a digitizer 210 for digitizing the electrical signals from camera 208.

The high powered microscope 204 (having a power ranging from 100× to 500×) magnifies the image of each event location along the wafer. These event locations can be viewed manually through eyepieces 206. The high resolution color video camera 208 mounted on microscope 204 converts the image from microscope 204 into electrical signals which are recorded by video recording unit 214. Video recording unit 214 can be either a video tape or a video disc recorder. The electrical signals from camera 208 are also displayed on color monitor 212. Monitor 212 enables the operator to visually inspect the events on the wafer without having to look through eyepieces 206.

Event discrimination system 200 provides flexibility in determining the nature of the event detected by event detection system 100. In the manual mode as described above, the nature of the detected event is determined visually by use of color monitor 212 and/or eyepieces 206. An operator views each event, and manually enters a corresponding event discrimination code into microprocessor storage via communications panel 400.

Figure 3:
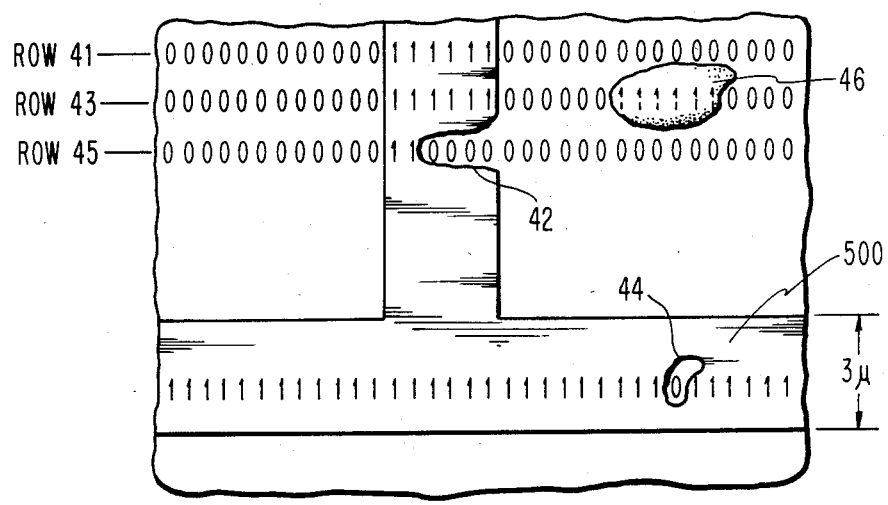
FIG. 3 is a top view of typical defects which occur on the surface of a processed wafer.

With reference to FIG. 3, the automatic mode of event discrimination will now be described.

FIG. 3 is a top view of several typical defects which occur on a processed wafer. Typically, the metallization stripes (or connecting lines) 500 have a width of 3 microns. Defect 42 is a "necking" defect, in which one side of a metal conducting line has an opening. Defect 44 is a "void", i.e., a region devoid of metal within the width of the conducting line. Finally, defect 46 is a particulate contaminant. Since these defects typically encompass a great percentage of the width of the conducting line, the resolution of the detection system should be on the order of 1.5 microns, or about one-half the minimum conducting line width of 3 microns. Obviously, the resolution of the system can be altered if it is found that the detection of larger or smaller defects is necessary. In order to produce a resolution of 1.5 microns, a resolution capability of 0.5 microns minimum pixel size is required.

Referring back to FIG. 1, digitizer 210 converts the image signals, on a pixel-by-pixel basis, into digital signals which are stored in microprocessor 300. Each pixel is stored in one memory location. Thus, the rows and columns of pixels are stored in respective rows and columns of memory.

After the image signals have been digitized and stored, they are processed using several techniques. First, the digitized image signals are compared to signals representative of a defect-free wafer (i.e., a "master die"). This is done in order to verify the existence of an event at the indicated location along the surface of the wafer. The master die image is stored on a hard storage medium (not shown) and is written into a RAM within microprocessor 300. As the event location is positioned under discrimination system 200, the corresponding location of the master die is read out from the RAM. In this manner, the master die and test wafer signals can be compared on a pixel-by-pixel basis.

Should any discrepancies be found between the master die signal and the test wafer signal, an image analysis algorithm is then performed in order to determine the nature of the detected event. For the purposes of illustration with reference to FIG. 3, assume that the image of the metal lines is digitized and stored as a series of "1"s, the defects 44 and 42 as well as the remaining wafer surface are stored as "0"+s, and defect 46 is digitized as "1"s. Since each pixel is 0.5 microns wide, six "1"s represent the width of a connection line 500 as in Row 41.

The stored test wafer image is read out and analyzed on a row-by-row basis. As each row is read out, the 0-1 and 1-0 transitions are determined. These transitions mark the beginning and end points of the width of a metal line, as well as the beginning and end points of any particulate contaminants (see Row 43). Within each set of 0-1 and 1-0 transitions, the number of "1"s is determined. If there are less than six "1"s, the event is characterized as a pattern defect (recall that a metal line should be six "1"s wide). For example, with reference to Row 45, note that only two "1"s are detected, thus indicating a pattern defect. This procedure is repeated row-by-row and column by-column basis in order to determine the nature of events at all surface locations.

For any subsequent pair of transitions noted during row-by-row or column-by-column read-out, the number of "1"s therebetween is counted. Once all of the rows (and/or columns) have been processed, the number of "1"s within these subsequent pairs of transitions are determined. If there are less than 100 "1"s, the defect can be identified as a particulate contaminant. That is, since the minimum size of an intended structure (a via hole) is on the order of 10 microns×10 microns, anything smaller is probably a contaminant.

The foregoing image analysis algorithm is given by way of example. Modifications can be made to the algorithm in order to accoun for variations in the width of the metal layers, the size of the particulate contaminants, etc.

As the above image analysis is performed on a given event, the applicable event discrimination code is automatically entered into the RAM. After all of the detected events (as represented by the stored X, Y event address signals) have been viewed and characterized by even discrimination system 200, the wafer is automatically conveyed to a second wafer storage cassette (not shown). After event discrimination, the X, Y event address signals (along with the corresponding wafer identification and event discrimination codes) are computer recorded by a host computer for offline analysis and interpretation.

As stated previously, an important feature of the present invention is that the entire wafer lot (i.e., 100% of the processed wafers) are scanned for defects. If the detection systems of the prior art were used in this manner, an impractical level of data storage would be needed.

While the invention has been particularly shown and described with reference to a preferred embodiment thereof, it will be understood by those skilled in the art that various changes in detail may be made therein without departing from the spirit, scope and teachings of the invention. Accordingly, the apparatus and method herein disclosed are to be considered merely as illustrative, and the invention is to be limited only as specified in the claims.

We claim:

1. A method of automatically inspecting the surface of a metallized semiconductor wafer, having features metallized thereon, for metallization defects and determining the nature of the detected defects, comprising the steps of:
orienting four light sources about the wafer, said light sources defining the sides of a square and said sides being oriented at 45° with respect to the features on the wafer surface;
transmitting light from the light sources onto sequential locations along the surface of the wafer;

forming an optical image of said sequential locations along the surface of the wafer;
converting said optical image into a first electrical signal;
comparing said first electrical signal to at least one threshold value;
recording the location of the wafer when said first electrical signal indicates, by comparison with said threshold value, that a metallization defect is present thereon;
automatically positioning the wafer beneath a high resolution microscope in accordance with the recorded locations of the wafer;
producing an optical signal corresponding to the image of said recorded wafer locations;
converting said optical signal into a second electrical signal, said second electrical signal being received by analog video display means;
digitizing said second electrical signal;
comparing said digitized electrical signal to a stored digitized master die signal in order to verify the existence of metallization defects at said recorded wafer locations; and
analyzing said digitized electrical signal to determine the nature of the metallization defect when said digitized electrical signal differs from said digitized master die signal.

2. The method as recited in claim 1, wherein said step of recording the location of the wafer from which the optical image is currently being received further comprises the steps of:
initiating a discrimination procedure when the level of said first electrical signal falls between a high threshold value and a low threshold value; and
continuing said discrimination procedure until the level of said first electrical signal rises above the threshold value or falls below the low threshold values.

3. In an optical inspection method for detecting metallization defects on a semiconductor surface having features metallized thereon wherein light is applied to the wafer surface at an oblique grazing angle and the intensity of said light is monitored, the improvement comprising:
orienting four light sources about the wafer, said light sources defining the sides of a square and said sides being oriented at 45° with respect to the features on the wafer surface.

* * * * *